(12) United States Patent
Chatterjea et al.

(10) Patent No.: US 11,087,888 B2
(45) Date of Patent: Aug. 10, 2021

(54) MONITORING DIRECT AND INDIRECT TRANSMISSION OF INFECTIONS IN A HEALTHCARE FACILITY USING A REAL-TIME LOCATING SYSTEM

(71) Applicant: KONINKLIJKE PHILIPS N.V., Eindhoven (NL)

(72) Inventors: Supriyo Chatterjea, Eindhoven (NL); Evert Jan Van Loenen, Waalre (NL); Anindita Chatterjea, Best (NL)

(73) Assignee: Koninklijke Philips N.V., Eindhoven (NL)

( * ) Notice: Subject to any disclaimer, the term of this patent is extended or adjusted under 35 U.S.C. 154(b) by 78 days.

(21) Appl. No.: 16/633,039

(22) PCT Filed: Jul. 19, 2018

(86) PCT No.: PCT/EP2018/069575
§ 371 (c)(1),
(2) Date: Jan. 22, 2020

(87) PCT Pub. No.: WO2019/020477
PCT Pub. Date: Jan. 31, 2019

(65) Prior Publication Data
US 2020/0176124 A1    Jun. 4, 2020

Related U.S. Application Data

(60) Provisional application No. 62/537,996, filed on Jul. 28, 2017.

(51) Int. Cl.
*G16H 50/80* (2018.01)
*G06K 7/10* (2006.01)
(Continued)

(52) U.S. Cl.
CPC ......... *G16H 50/80* (2018.01); *G06K 7/10366* (2013.01); *G06K 7/12* (2013.01); *G06K 19/0723* (2013.01)

(58) Field of Classification Search
CPC ...... G16H 50/80; G06K 7/10366; G06K 7/12; G06K 19/0723
(Continued)

(56) References Cited

U.S. PATENT DOCUMENTS 10,503,347 B2 * 12/2019 Humayun ............... G06Q 50/01
2007/0106775 A1 * 5/2007 Wong .................... G01S 5/0284
709/223
(Continued)

FOREIGN PATENT DOCUMENTS

JP         05806850 B2   11/2015
JP       2016184196 A   10/2016
(Continued)

OTHER PUBLICATIONS

Scott, RD II, "The direct medical costs of healthcare-associated infections in U.S. hospitals and the benefits of prevention". Diseases CCfl, ed.: Centers for Disease Control and Prevention: 1-13.
(Continued)

*Primary Examiner* — Michael G Lee
*Assistant Examiner* — David Tardif

(57) ABSTRACT

An infectious disease transmission tracking system (10) includes a real-time locating system (RTLS) (12) configured to track locations of tags (14, 15) in a monitored area. At least one electronic processor (22) is in operative communication with the RTLS to receive locations of tags in the monitored area. A non-transitory storage medium stores, a map (30) of the monitored area; a nodes database (32) storing information on nodes (18) in which each node is a
(Continued)

person, a mobile object, or a map zone and the nodes database stores information on the nodes including at least (i) an identification of each node as a person, a mobile object, or a map zone, (ii) an identification of a tag associated with each node that is identified as a person or a mobile object, (iii) locational information on the map for each node that is identified as a map zone, and (iv) an infection likelihood for each node with respect to a tracked pathogen; and a pathogen database (34) storing infectious transmission information for at least the tracked pathogen including one or more transmission modes for the tracked pathogen and at least one node residency time for the tracked pathogen. The non-transitory storage medium includes instructions readable and executable by the at least one electronic processor to perform an infectious disease transmission tracking method (100) including: computing a pathway (35) on the map of at least one infected node using locations of the tag associated with the infected node received from the RTLS wherein an infected node has a non-zero infection likelihood respective to the tracked pathogen which satisfies an infected criterion; computing an infectious zone (36) on the map along the pathway using the infectious transmission information stored in the pathogen database; for each node contacting the infectious zone, adjusting the infection likelihood of the contacting node in the nodes database based on at least the infectious transmission information for the tracked pathogen and designating the contacting node as an infected node if the updated infection likelihood of the contacting node satisfies the infected criterion.

15 Claims, 5 Drawing Sheets

(51) Int. Cl.
*G06K 7/12* (2006.01)
*G06K 19/07* (2006.01)

(58) Field of Classification Search
USPC .............................................................. 700/2
See application file for complete search history.

(56) References Cited

U.S. PATENT DOCUMENTS

| | | | |
|---|---|---|---|
| 2012/0112883 A1* | 5/2012 | Wallace | G16H 40/67 340/10.1 |
| 2014/0167917 A2 | 6/2014 | Beach et al. | |
| 2017/0024531 A1* | 1/2017 | Malaviya | G16H 40/63 |
| 2019/0148023 A1* | 5/2019 | Sadilek | G06N 20/00 705/2 |
| 2021/0014654 A1* | 1/2021 | Gupta | H04L 67/10 |

FOREIGN PATENT DOCUMENTS

| | | |
|---|---|---|
| WO | 2010066033 A1 | 6/2010 |
| WO | 2010099488 A1 | 9/2010 |

OTHER PUBLICATIONS

"Practical Guidelines for Infection Control in Health Care Facilities", Jan. 1, 2004. https://www.who.int/westernpacific.
International Search Report—PCT/EP2018/069575 dated Jul. 19, 2018.
http://www.cdc.gov/HAI/surveillance/.
http://www.who.int/gpsc/country_work/gpsc_ccisc_fact_sheet_en.pdf.
http://www.wpro.who.int/publications/docs/practical_guidelines_infection_control.pdf.
http://www.who.int/csr/resources/publications/WHO_CDS_EPR_2007_6c.pdf.
http://www.nhs.uk/chq/Pages/how-long-do-bacteria-and-viruses-live-outside-the-body.aspx.
http://www.ncbi.nlm.nih.gov/pubmed/20553340.
Disease Mapping and Infection Control System and Method: https://www.google.com/patents/US20120112883.

* cited by examiner

MONITORING DIRECT AND INDIRECT TRANSMISSION OF INFECTIONS IN A HEALTHCARE FACILITY USING A REAL-TIME LOCATING SYSTEM

CROSS-REFERENCE TO PRIOR APPLICATIONS

This application is the U.S. National Phase application under 35 U.S.C. § 371 of International Application No. PCT/EP2018/069575, filed on Jul. 19, 2018, which claims the benefit of U.S. Patent Application No. 62/537,996, filed on Jul. 28, 2017. These applications are hereby incorporated by reference herein.

FIELD

The following relates generally to the patient monitoring arts, patient treatment facility monitoring arts, infection containment arts, tracking system arts, and related arts.

BACKGROUND

Infection control is the discipline concerned with combating hospital acquired or healthcare-associated infection (HAI). HAI is an infection whose development is favored by a hospital environment, nursing home, rehabilitation facility, clinic, or other clinical settings. This infection is spread to the patient in the clinical setting by a number of means. Health care staff can spread infection, contaminated equipment, bed linens, or air droplets. The infection can originate from another infected patient or hospital staff member, or in some cases, the source of the infection cannot be determined.

According to the Centers for Disease Control and Prevention in the U.S., there were an estimated 722,000 HAI incidents in U.S. acute care hospitals in 2011. About 75,000 hospital patients with HAIs died during their hospitalizations. More than half of all HAIs occurred outside of the intensive care unit (see, e.g., http://www.cdc.gov/HAI/surveillance/). Preventing HAIs could save $25-32 billion in the US alone (see, e.g., Scott RD II, "The direct medical costs of healthcare-associated infections in U.S. hospitals and the benefits of prevention", in Diseases CCfI, ed.: Centers for Disease Control and Prevention: 1-13).

Most countries lack surveillance systems for health care-associated infections. Those that do have systems often struggle with the complexity and lack of standardized criteria for diagnosing the infections. While this makes it difficult to gather reliable global information on health care-associated infections, results from studies clearly indicate that each year, hundreds of millions of patients are affected by health care associated infections around the world (see, e.g., http://www.who.int/gpsc/country_work/gpsc_ccisc_fact_sheet_en.pdf). Moreover, recent outbreaks of infectious diseases such as Ebola, MERS, SARS and H1N1 have highlighted the need by healthcare institutions to follow proper infection control protocols.

The World Health Organization (WHO) has strict guidelines on protocols that need to be followed to minimize the risk of the spread of infection (see, e.g., http://www.wpro.who.int/publications/docs/practical_guidelines_infection_control.pdf; and http://www.who.int/csr/resources/publications/WHO_CDS_EPR_2007_6c.pdf). While some of the guidelines are easy to implement and follow, there are others that are hard to implement. For example, there are protocols that require a healthcare worker to follow a different set of protocols when the distance between the worker and an infected patient is less than 1 meter. Apart from adhering to such distance restrictions based on visual observations, hospitals today do not utilize any monitoring systems to ensure that the recommended protocols are strictly implemented. Furthermore, in the event of an infectious disease breakout, the usual approach to trace the movements of all individuals who may have come in contact with the infected patient is purely based on memory.

A Real-Time Locating System (RTLS) can be used to track individual patients and healthcare workers for the purpose of infection control. Previous efforts have been made regarding aspects of this compliance (see, e.g., US Pat. Pub. No. 2012/0112883).

The following discloses new and improved systems and methods.

SUMMARY

In one disclosed aspect, an infectious disease transmission tracking system includes a real-time locating system (RTLS) configured to track locations of tags in a monitored area. At least one electronic processor is in operative communication with the RTLS to receive locations of tags in the monitored area. A non-transitory storage medium stores, a map of the monitored area; a nodes database storing information on nodes in which each node is a person, a mobile object, or a map zone and the nodes database stores information on the nodes including at least (i) an identification of each node as a person, a mobile object, or a map zone, (ii) an identification of a tag associated with each node that is identified as a person or a mobile object, (iii) locational information on the map for each node that is identified as a map zone, and (iv) an infection likelihood for each node with respect to a tracked pathogen; and a pathogen database storing infectious transmission information for at least the tracked pathogen including one or more transmission modes for the tracked pathogen and at least one node residency time for the tracked pathogen. The non-transitory storage medium includes instructions readable and executable by the at least one electronic processor to perform an infectious disease transmission tracking method including: computing a pathway on the map of at least one infected node using locations of the tag associated with the infected node received from the RTLS wherein an infected node has a non-zero infection likelihood respective to the tracked pathogen which satisfies an infected criterion; computing an infectious zone on the map along the pathway using the infectious transmission information stored in the pathogen database; for each node contacting the infectious zone, adjusting the infection likelihood of the contacting node in the nodes database based on at least the infectious transmission information for the tracked pathogen and designating the contacting node as an infected node if the updated infection likelihood of the contacting node satisfies the infected criterion.

In another disclosed aspect, a non-transitory computer-readable storage medium includes a map database storing a map of a monitored area. A nodes database stores information on nodes in which each node is a person, a mobile object, or a map zone and the nodes database stores information on the nodes including at least (i) an identification of each node as a person, a mobile object, or a map zone, (ii) an identification of a tag associated with each node that is identified as a person or a mobile object, (iii) locational information on the map for each node that is identified as a map zone, and (iv) an infection likelihood for each node with respect to a tracked pathogen. A pathogen database stores infectious transmission information for at least the tracked pathogen including one or more transmission modes for the tracked pathogen and at least one node residency time for the tracked pathogen. The storage medium also includes instructions readable and executable by at least one electronic processor to perform an infectious disease transmission tracking method including: receiving, from one or more tag readers of a real time location system (RTLS), locations of one or more tags of the RTLS in the monitored area; computing a pathway on the map of at least one infected node using locations of the tag associated with the infected node received from the RTLS in which an infected node has a non-zero infection likelihood respective to the tracked pathogen which satisfies an infected criterion; computing an infectious zone on the map along the pathway using the infectious transmission information stored in the pathogen database; for each node contacting the infectious zone, adjusting the infection likelihood of the contacting node in the nodes database based on at least the infectious transmission information for the tracked pathogen and designating the contacting node as an infected node if the updated infection likelihood of the contacting node satisfies the infected criterion.

In another disclosed aspect, an infectious disease transmission tracking system includes a real-time locating system (RTLS) including tags and tag readers in which the tag readers are distributed through a monitored area and are configured to track locations of the tags in the monitored area. At least one electronic processor is in operative communication with the RTLS to receive locations of tags in the monitored area. A non-transitory storage medium stores a map of the monitored area. A nodes database stores information on nodes in which each node is a person, a mobile object, or a map zone and the nodes database stores information on the nodes including at least (i) an identification of each node as a person, a mobile object, or a map zone, (ii) an identification of a tag associated with each node that is identified as a person or a mobile object, (iii) locational information on the map for each node that is identified as a map zone, and (iv) an infection likelihood for each node with respect to a tracked pathogen. A pathogen database stores infectious transmission information for at least the tracked pathogen including one or more transmission modes for the tracked pathogen and at least one node residency time for the tracked pathogen. The storage medium includes instructions readable and executable by the at least one electronic processor to perform an infectious disease transmission tracking method including: computing a pathway on the map of at least one infected node using locations of the tag associated with the infected node received from the RTLS wherein an infected node has a non-zero infection likelihood respective to the tracked pathogen which satisfies an infected criterion; computing an infectious zone on the map along the pathway using the infectious transmission information stored in the pathogen database; for each node contacting the infectious zone, adjusting the infection likelihood of the contacting node in the nodes database based on at least the infectious transmission information for the tracked pathogen and designating the contacting node as an infected node if the updated infection likelihood of the contacting node satisfies the infected criterion, the adjusting of the infection likelihood of the contacting node in the nodes database being determined by the equation: $p=f(d, a, t, s, T, H, o, i, h)$, where d is a distance between two nodes; a is air flow characteristics between the two nodes; t is a time passed since one of the nodes was last in contact with the pathogen of interest; s is a type of surface of the node, T is a temperature in the vicinity of the node; H is a humidity value in the vicinity of the node; o is an order of node from the node which is considered to be the original source of infection; I is a number of times that the nodes have encountered each other since first getting infected; and h is an execution of hygiene regime.

One advantage resides in providing an improved RTLS-based infectious disease transmission tracking or monitoring system that addresses spatial and temporal aspects of infectious disease management.

Another advantage resides in providing an RTLS-based infectious disease transmission tracking or monitoring system with improved fidelity to WHO guidelines for infection control.

Another advantage resides in providing an RTLS-based infectious disease transmission tracking or monitoring system that generates quantifiable data regarding the spread of an infection, rather than word of mouth testimony from hospital staff.

Another advantage resides in providing an RTLS-based infectious disease transmission tracking or monitoring system that provides an RTLS system with contact tracing infection data, rather than data from medical records.

Another advantage resides in providing an RTLS-based infectious disease transmission tracking or monitoring system to track the spread of infections by computing a risk of infection in real time including taking into account different disease transmission pathways with different spatial ranges.

Another advantage resides in providing an RTLS-based infectious disease transmission tracking or monitoring system to dynamically track the spread of infections by computing a risk of infection in real time including taking into account decreasing likelihood of infectious transmission in situations where a disease transmission vector has a limited pathogen viability lifetime.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the invention.

DETAILED DESCRIPTION

Figure 1:
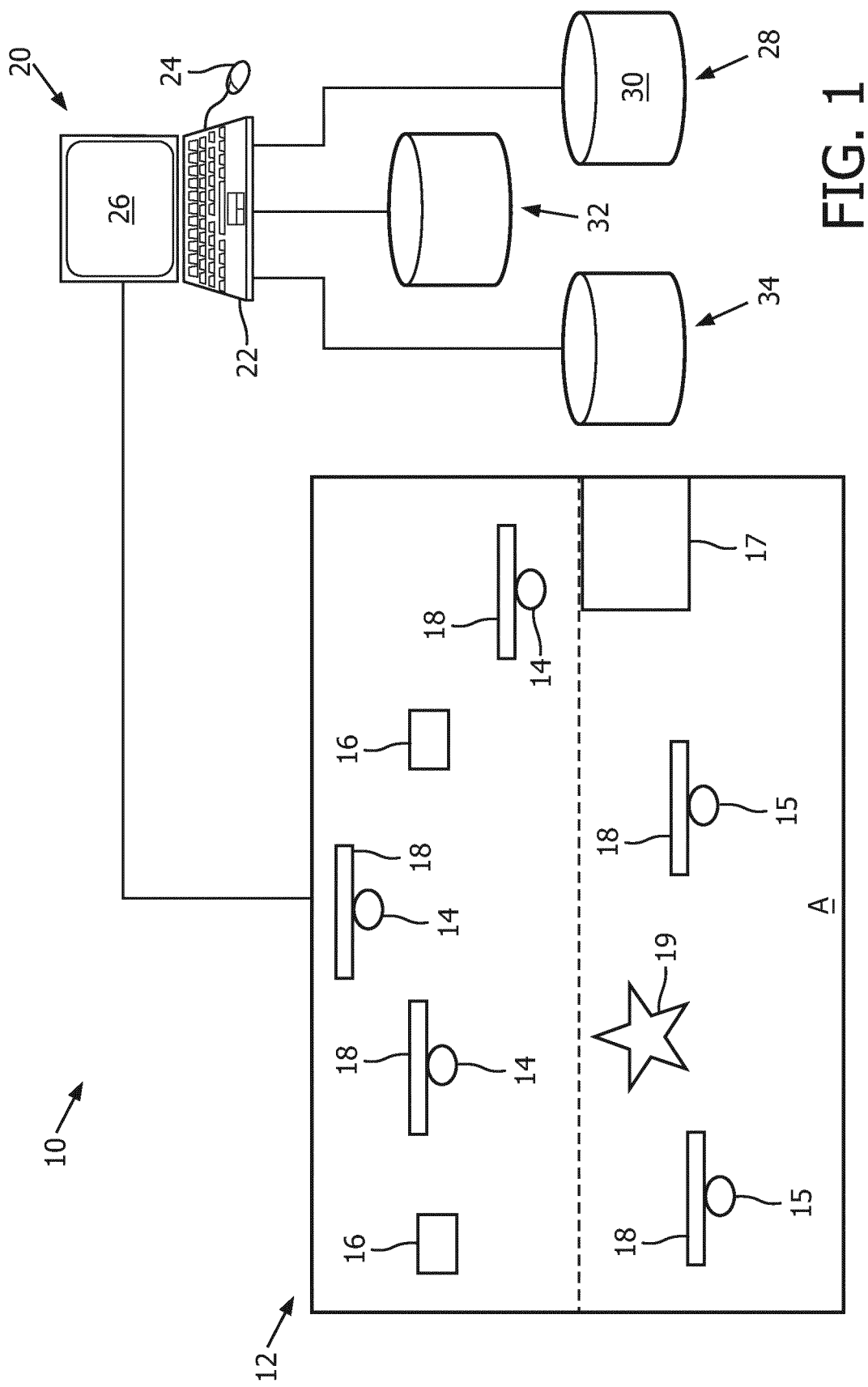
FIG. 1 diagrammatically shows a Real-Time Locating System (RTLS)-based infectious disease tracking system according to one aspect.

The following discloses approaches for tracking or monitoring of transmission of hospital (or healthcare facility)

acquired infection (HAI). The disclosed approaches employ a Real-Time Locating System (RTLS) for spatially and temporally mapping contact pathways.

The following more particularly relates to the tracing of contacts of an infected person in the hospital using an RTLS to track infected (or potentially infected) persons. RTLS are currently deployed in some hospitals for purposes such as tracking patients, monitoring deployment of medical resources such as mobile assets (e.g. mobile x-ray devices, beds), or so forth. In principle, an RTLS can be used to track an infected patient and identify other persons with whom the infected patient comes into contact; and then to track persons those individuals come into contact with, and so forth, so as to track the infectious transmission pathways of a pathogen during an infectious outbreak.

However, the use of RTLS for this purpose has certain difficulties. First, the RTLS has limited spatial resolution, which may vary by location. For example, the RTLS may identify the location of a patient with high spatial resolution in a patient hospital room, but with coarser resolution in hallways. The range of infectious transmission can also vary depending upon the transmission pathway (contact, airborne, or droplets), and the likelihood of transmission may depend on exposure time. Second, RTLS tracking of infected individuals does not take into account the potential for temporally delayed transmission. For example, if an infected person occupies a waiting room for some time interval and then leaves, and thereafter a nurse cleans the waiting room, that nurse may become infected, e.g. by way of pathogenic contamination of surfaces in the waiting room. Yet, the infected person and the nurse never came into contact or even close proximity to each other.

The disclosed approach overcomes these difficulties and others. The disclosed tracking estimates the most likely path of the patient, e.g. in hallways where the RTLS provides limited tracking. An infectious zone is defined along this path, e.g. one meter to either side of the path in the case of droplet transmission. The infectious zone may be adjusted based on additional information. For example, if the patient stays in a single location for some time, the zone may be expanded based on that extended occupancy, or may be expanded to fill the entire room.

The disclosed tracking approach also extends the concept of "transmission" to more broadly encompass transmission between pairs of "nodes", where a node may be a person, but also may be a location (i.e., spatial "zone") or an asset or other mobile object (e.g. a mobile x-ray device, patient bed, or so forth). Thus, when a patient occupies a waiting room there will be a transmission likelihood from the patient to the waiting room; when the nurse later cleans the waiting room there will be a transmission likelihood from the waiting room to the nurse. The transmission tracking is also dynamic based on known time constraints on transmission. Thus, for example, if a known pathogen can contaminate surfaces which then remain infectious for two hours, then the waiting room may have its likelihood of infection reset to zero after two hours (and optionally its likelihood of infection may be set to decay to zero as a function of time to even more accurately represent the actual transmission probability over time).

Other available information can also be taken into account in dynamic tracing of infectious contact pathways. For example, some RTLS have the capability to monitor usage of sanitation devices such as sanitary soap dispensers. If this is available, then if a nurse interacts with a patient in the hospital room and the sanitary device in the patient's hospital room is not used, this information from the RTLS can be used to increase the likelihood of infectious transmission to the nurse. Temperature and/or humidity may be monitored automatically, and this information may be taken into account in estimating the transmission likelihood (for example, if residency of a known pathogen on surfaces is humidity-dependent). As another example, if two nodes are connected by an HVAC circuit that does not have HEPA filters capable of filtering out the pathogen, then the likelihood of infection between these nodes may be increased based on this information.

Embodiments of the disclosed infectious contact tracking system include various components. The RTLS may be embodied by a tag/reader system employing RFID, WiFi, infrared, ultrasound, or other tag reading technologies. A map of the hospital is provided, including delineation of the spatial zones monitored by the RTLS along with other salient information such as auxiliary monitoring stations (e.g. temperature sensors, humidity sensors, sanitary device usage sensors), types of surfaces in the room (relevant to surface-mediated transmission), HVAC circuit pathways, and/or so forth. A computer is programmed by instructions stored on a non-transitory storage medium (e.g. hard drive, optical disk, FLASH memory or other electronic storage medium, or so forth) and readable and executable by the computer to perform infectious contact tracing as outlined above using data from these devices. The output may, for example, be a list of nodes (persons, locations, and assets) with likelihoods of infection, which may be time-dependent. To promote rapid assessment of the most likely nodes to be infected, an infected criterion may be applied, by which only those nodes which satisfy the infected criterion are listed. It should be noted that in such an approach, the infected criterion should not be viewed as definitively identifying nodes which are infected, but rather should be viewed as identifying nodes whose likelihood of infection is sufficiently high that follow-up testing should be performed (e.g. testing the individual for the infection; swiping surfaces of the mobile object to test for pathogen contamination, performing testing of air in a spatial zone meeting the infected criterion, or so forth). Advantageously, using such an infected criterion provides identification of the persons, objects, and/or places most likely to be infected thereby providing a principled basis for efficient allocation of limited testing resources.

The RTLS systems of the following are described now in more detail. RTLS systems provide immediate or real-time tracking and management of medical equipment, staff and patients. This type of solution enables healthcare facilities to capture workflow inefficiencies, reduce costs, and increase clinical quality. RTLS systems are comprised of various tags (which may be referred to by other nomenclatures, e.g. as badges), platforms (Wi-Fi, Infrared, Ultrasound, and others), hardware infrastructure (tag readers and tag exciters, in the case of passive tags that must be externally energized) and other components (e.g. server computers and non-transitory storage medium storing software readable and executable by the server(s) to perform RTLS operations such as tracking tagged entities). Typically, an RTLS consists of either specialized fixed location sensors (i.e. tag readers) receiving wireless signals from small ID badges or other types of tags attached to equipment or persons, or fixed beacons (i.e. RF, infrared or ultrasound beacons) providing location information to ID badges or other types of tags attached to equipment or persons. Each tag transmits its own unique ID in real time, and depending on the technology chosen, the system locates the tags and therefore the location of the tagged entities. Depending on the solution, varying degrees of spatial granularity can be achieved. Basic RTLS solutions can enable tracking in a hospital's unit or floor, whereas clinical-grade systems may achieve finer spatial granularity on the level of room, bed, bay, and even shelf-level tracking. Moreover, the spatial granularity may vary for different locations depending upon the type and distribution/density of tag readers. For example, if one or more tag readers or beacons is installed in each patient room, which has relatively small spatial extent, then the tracking precision in patient rooms may be high. By contrast, a smaller density of tag readers or beacons may be deployed along hospital corridors, providing more coarse spatial resolution in corridors.

In the disclosed RTLS-based infectious disease transmission tracking or monitoring systems, the RTLS systems are used to track disease transmission with closer fidelity to WHO regulations regarding infectious disease control. The WHO outlines protocols to prevent the spread of infections by three different transmission pathways: direct contact; airborne transmission; and transmission by droplets. Contact precautions are designed to reduce transmission through direct patient contact and indirect contact with items in the patient's environment. Airborne precautions are designed to reduce the transmission of diseases spread by an airborne route in which transmission occurs when droplets having nuclei of less than 5 micron in size are disseminated in the air. These particles can remain suspended in the air for long periods of time. Droplet precautions are designed to reduce transmission of disease by adequate contact between a susceptible person and large particle droplets (i.e., greater than 5 microns). These droplets are usually generated from the infected person during coughing or sneezing. Large particles typically remain suspended in the air for limited period of time and settle within 1 m of the source.

When taking these precautions into account, it is evident that an infection can spread through: (1) direct physical contact with the infected patient; (2) immediate contact over air due to close proximity (may also be shared ventilation between rooms); (3) delayed contact with air that has been infected by infected patient; (4) indirect physical contact with an individual who has been in direct physical contact with the infected patient; and (5) indirect physical contact with an object which has been in direct physical contact with the infected patient. Apart from the first two modes of spreading infection, which occur instantaneously, the remaining methods involve the spread of infection over an extended duration of time. For example, an object that has been touched by an infected patient might remain infectious for the next five hours. It should also be noted that a given pathogen may be transmittable via only a subset of these pathways, e.g. some pathogens cannot be transmitted by airborne transmission; and moreover, the infectious lifetime for a given delayed pathway depends on the type of pathogen and the type of environmental conditions the pathogen is exposed to.

In the event of the spread of an infection or the outbreak of an infectious disease, it is important for hospital administrators to know several factors, including the source of the infection, the manner in which the infection spread, the individuals responsible for spreading the infection, the individuals who are currently infected (or have a high likelihood of being infected), the time at which a particular individual became infected, portions of a hospital that need to be disinfected, among others. In order to determine these factors, most hospital administrators depend on their pre-existing knowledge of the various workflows/processes within the hospital. They also might refer to hospital records which contain information about patients and clinical/non-clinical staff who were involved in caring for the infected individual. Interviews are also performed with all patients and caregivers who may have interacted with each other at some point in the past in order to trace all possible points of contact through which the infection may have spread.

There are several problems with this approach. First, contact tracing is based on highly coarse-grained data (e.g. information gathered from interviews is purely based on memory). Second, gathering information from medical records is also not granular enough to provide contact tracing data that is accurate enough to easily track how an infection has spread or which rooms in a hospital need to be disinfected. Third, pathogens can survive outside the body for extended time periods. This means that a room can remain infected long after the source of infection has left the room. This makes contact tracing based on information derived from interviews (i.e. memory) extremely difficult. Fourth, it is impossible to track the spread of infections or compute the risk of infection spread in real-time.

With reference to FIG. 1, an illustrative infectious disease transmission tracking system 10 is shown. The tracking system 10 includes a real-time locating system (RTLS) 12 with radiofrequency identification (RFID) tags 14 and RFID tag readers 16. The tag readers 16 are distributed through a monitored area A and are configured to track locations of the tags 14 in the monitored area. For example, the tags 14 are attached or otherwise secured to one or more nodes 18 (e.g., a patient, a medical professional, a mobile object such as a piece of medical equipment, a zone in the monitoring area A, and the like). The tags 14 may be referred to by other terms, e.g. badges, tracking chips, et cetera—the term "tag" as used herein is intended to encompass such alternative nomenclatures. The tag readers 16 are distributed throughout the monitored area A where persons or mobile objects to be tracked may traverse (e.g., in a patient room, in a hallway, at a workstation of a medical professional, and the like). In some examples, the monitored area A can be a two-dimensional area (i.e., a single floor of a hospital) while in other examples, the monitored area can be a three-dimensional area (i.e., multiple floors of a hospital). The tag readers 16 are configured to receive location data from the corresponding tags 14, thereby allowing the tag readers to track a corresponding node 18. In the simplest design, a tag reader may have an operational range, e.g. five meters, and any tag detected by that tag reader is known to be within a five meter radius of the tag reader. In other designs, two or three or more tag readers with overlapping operational ranges may operate in concert to more precisely locate a tag, e.g. using triangulation or the like. In yet other designs, a single tag reader may provide directional information using a phased array transducer, a rotating transducer, or so forth. These are merely illustrative examples of RTLS ranging and angulating technologies, and more generally the RTLS 12 may use any suitable tracking technology to provide real time locational information for the tags present in the monitored area A. In addition, the tag readers 16 are configured to receive tag identifying information from the corresponding tag 14 in order to determine the particular tag 14 (and hence the corresponding node 18) being tracked.

The tag identifying information may take various forms, e.g. in active tag designs the tag 14 includes an on-board battery-powered microprocessor or microcontroller and associated non-transitory memory (e.g. a FLASH, PROM, or other electronic memory chip) that stores a tag identifier number or the like which the tag 14 transmits to the tag reader 16. In a passive tag design, radio frequency energy transmitted by the tag reader 16 to the tag 14 powers the tag to drive it to transmit its tag identifier. In less sophisticated designs, each tag may transmit at a different frequency and the tag is identified by its response frequency. These are merely illustrative examples of tag identification technologies, and more generally the RTLS 12 may use any suitable tag identification technology to provide the tag readers 16 with real time identification of detected/tracked tags. Optionally, the RTLS 12 may be compliant with an industry-defined RTLS standard, e.g. ISO/IEC 24730-1 or a variant thereof.

In other embodiments, the RTLS 12 can include an infrared identification (IRID) system including one or more tags 15; a beacon or tag reader 17; a radiofrequency tracking communication station 19; and a server 21. The tags 15 are configured to be worn by a hospital staff member or a patient or attached to a node 18. The tags 15 include an IR receiver and RF transceiver (not shown). The beacon 17 is configured for attachment to a ceiling of the monitoring area A and covers a particular zone in the monitoring area by broadcasting an IR signal. The beacon 17 is configured to broadcast an IR signal with a unique ID representing a particular zone. An identification (ID) is mapped to a particular zone in the monitoring area A. The communication station 19 is configured to communicate with the tags 15 via RF signals. In use, the beacon 17 is configured to broadcast a unique IR ID representing a zone in the monitoring area A. The corresponding tag 15 in the zone receives the IR ID from the beacon 17 via the IR receiver. The tag 15 is configured to report the sensed IR ID to the communication station 19 via an RF signal. The star 19 is configured to report the IR ID to the server 21, which is configured to map the IR ID to the corresponding zone (which can be set by an installer of the RTLS 12). In other embodiments, the RTLS 12 can include any other location identification system, for example using RF, ultrasound, infrared or vision technology.

The illustrative infectious disease transmission tracking system 10 also includes a computer or imaging workstation or other electronic data processing device 20 with typical components, such as at least one electronic processor 22, at least one user input device (e.g., a mouse, a keyboard, a trackball, a device with an embedded screen such as a tablet, a smartphone, a smartwatch, an alternate reality/virtual reality headset or goggles, and/or the like) 24, and a display device 26 on which an interactive abnormality/lesion insertion graphical user interface (GUI) (not shown) can be displayed. In some embodiments, the display device 26 can be a separate component from the computer 20.

The at least one electronic processor 22 is operatively connected with a non-transitory storage medium (not shown) that stores instructions which are readable and executable by the at least one electronic processor 16 to perform an infectious disease transmission tracking method or process 100, and to perform other operations as appropriate (e.g. data acquisition from the RTLS 12). The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth. In some examples, the infectious disease transmission tracking method or process 100 may be performed by cloud processing.

The non-transitory storage medium can include one or more databases. For example, the non-transitory storage medium stores a map database 28 containing a map 30 of the monitored area A. The map 30 can include a floorplan layout of a hospital, and may also include information such as HVAC linkages between spatial zones, information on sanitary dispenser monitors (if monitored by the RTLS 12), and so forth.

The non-transitory storage medium further stores a nodes database 32 containing information related to the nodes 18. The nodes 18 can be of three types in the illustrative embodiment: patient and staff nodes, mobile object nodes such as a piece of medical equipment, and map zone nodes corresponding to spatial zones or areas defined in the monitoring area A (or in the map 30 of that area A). Advantageously, and as further detailed herein, providing for these three types of nodes enables tracking of infectious pathogen transmission via direct contact (by tracking intersections of nodes representing an infected person and a contacting person), via surface mediation (by tracking contact of an infected person with a mobile object node and subsequent contact of the mobile object node with a second person), or via airborne or droplet pathways (by tracking contact of an infected person with a map zone node and subsequent contact of a second person with that map zone node). As used herein, the term "mobile unit" or "mobile object" (and variants thereof) refer to objects expected to occasionally move from one spatial zone to another, for example by being carried by a person. Examples of mobile objects include various medical assets such as mobile x-ray units, mobile ultrasound machines, intravascular delivery systems that can be expected to occasionally be moved from one patient room to another, feeding pumps, infusion pumps, or so forth. In addition, the nodes database 32 may store information related to types of mobile objects so as to estimate residency of the pathogen on the surface. For example, an object with shiny metal surfaces may have a much shorter pathogen residency than an object with porous surfaces. In addition, as used herein, a zone in the monitoring area A (i.e., a map zone) refers to be an entire room or a portion of a room of a hospital, or may be some other spatial zone such as a hallway. In addition, these zones may be classified according to location in the monitoring area A. The choices or delineations of map zones for the purpose of pathogen transmission tracking is dependent upon factors such as the spatial resolution of the RTLS 12, natural spatial delineations defined by architecture (e.g. a small room may sensibly be chosen as a single map zone) or usage (e.g. in a waiting room it may make sense to define the waiting area containing the patient chairs as one map zone and the receptionist area as a different map zone), or so forth.

The nodes database 32 stores information related to the nodes 18. In one example, the nodes database 32 stores information related to an identification of each node 18 as a person, a mobile object, or a map zone. In another example, the nodes database 32 stores information related to an identification of a tag 14 associated with each node 18 that is identified as a person or a mobile object. In a further example, the nodes database 32 stores locational information on the map 30 for each node 18 that is identified as a map zone. In yet another example, the nodes database 32 stores information related to an infection likelihood for each node with respect to a tracked pathogen. In some embodiments, the infection likelihood can be a continuous or stepped value ranging between zero and one, with a value of one being indicative of near-certain infection and a value of zero being indicative of near certainty of no infection, and an intermediate value such as 0.7 being indicative of an intermediate likelihood of infection. In other embodiments, the infection likelihood can be a binary value of either zero (not infected) or one (infected).

In a further example, the non-transitory storage medium can include a pathogen database 34 configured to store transmission information for at least a tracked pathogen. The transmission information can include one or more transmission modes (e.g., contact, airborne, droplets, and the like) for the tracked pathogen. As used herein, the term "pathogen" (and variants thereof) refers to a single pathogen, a class of pathogens, or an unknown pathogen that is assigned conservative estimate values for the transmission information in the pathogen database 34 (i.e., conservative being likely to overestimate infection likelihoods). If a given pathogen is not capable of transmission by a particular pathway (e.g. cannot be transmitted by the airborne pathway) then the pathogen database 34 suitably stores this information. In addition the pathogen database 34 is configured to store at least one node residency time for the tracked pathogen. The residency time, in some examples, can be a function of the transmission mode. For example, a pathogen may have a (typically longer) airborne contamination residency time versus a (typically shorter) droplet contamination residency time, and may have some other residency time for surface contamination (which may be further divided based on the type of surface). In other examples, the residency time can be dependent on further information about the nodes 18 stored in the nodes database 32. In further examples, the residency time can be a function of temperature and humidity (among other factors), as well as different types of nodes 18 (i.e. persons, objects, or zones) that naturally have different residency times. The information on pathogens stored in the pathogen database 34 is preferably derived from the professional epidemiology literature, and may be occasionally updated to reflect the most current medical knowledge. In some examples, pathogen information can be entered into the pathogen database 34. For example, a user may enter this pathogen information if the user suspects that there has been an infection outbreak in instances where the hospital hasn't experience problems with a particular pathogen before and is experiencing the pathogen for the first time.

It will be appreciated that the workstation 20 can be in electronic communication with one or more other databases (not shown) (e.g., an electronic medical record (EMR) database, a picture archiving and communication system (PACS) database, and the like), among others. In addition, these databases 30, 32, 34 may be a single database, or a pair of databases.

As shown in FIG. 1, the electronic processor 22 is programmed to perform RTLS-based infectious disease transmission tracking. For example, the electronic processor 22 is in operative communication with the RTLS 12 to receive locations of the tags 14 in the monitored area A from the tag readers 16 of the RTLS. The non-transitory medium includes instructions readable and executable by the at least one electronic processor 22 to perform an infectious disease transmission tracking method 100. In some embodiments, the same electronic processor 22 also performs implementation of software components of the RTLS 12; while in other embodiments software components of the RTLS 12 are implemented on a different computing device or system (not shown).

Figure 2:
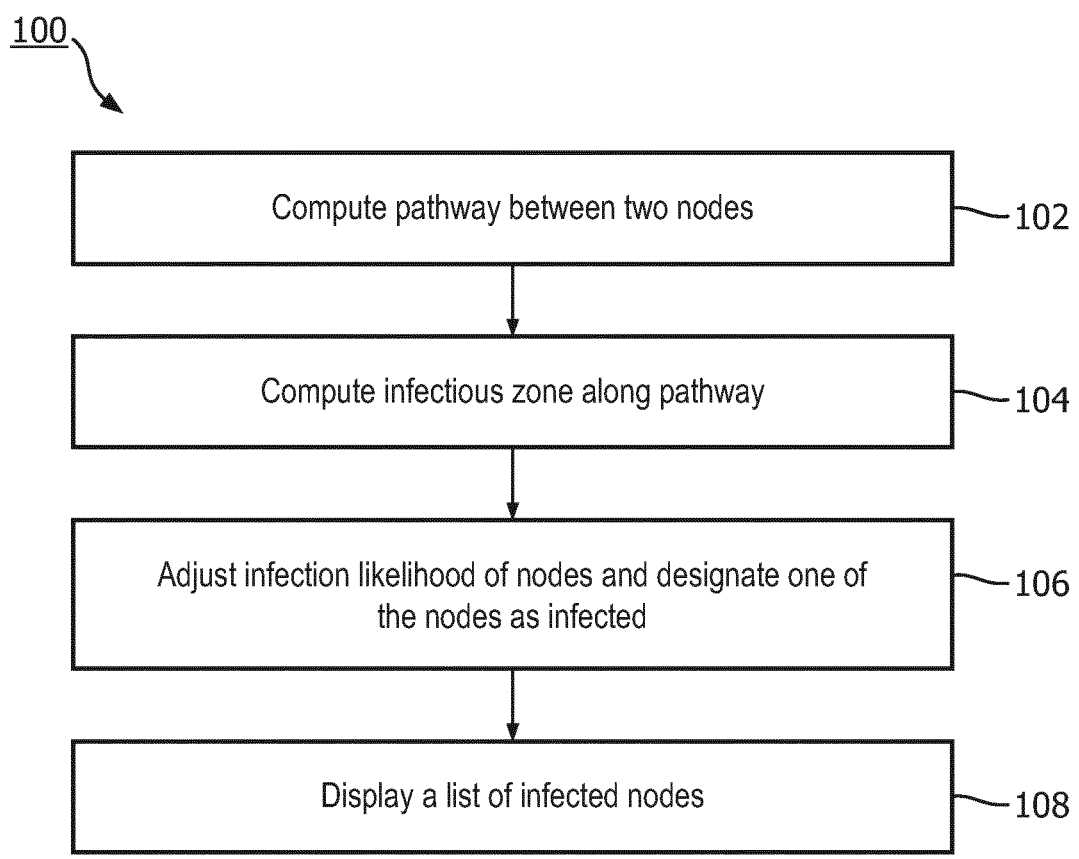
FIG. 2 shows an exemplary flow chart depicting aspects of operation of the system of FIG. 1.
Figure 4:
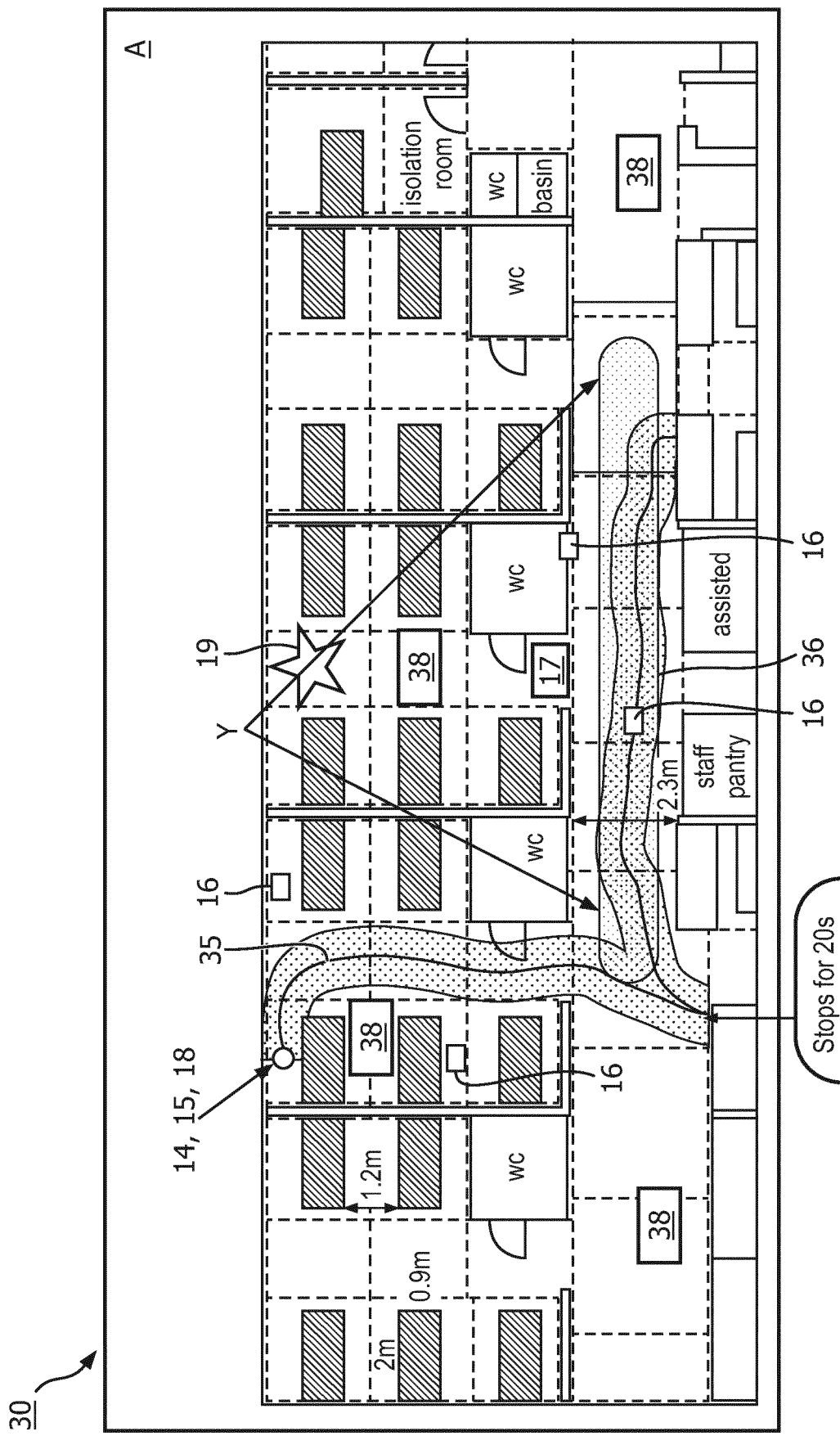
FIG. 4 illustratively shows another example use of the tracking system of FIG. 1.

With reference now to FIG. 2 and with continuing reference to FIG. 1, an illustrative embodiment of the infectious disease transmission tracking method 100 is diagrammatically shown as a flowchart. At 102, a pathway is computed on the map 30 of at least one infected node 18 using locations of the tag 14 associated with an infected node received from the RTLS 12. For example, an infected node 18 has a non-zero infection likelihood respective to the tracked pathogen which satisfies an infected criterion. In some examples, the infected criterion can involve a user (e.g., a medical professional) selecting, via the use input device 24 the infected node 18 in the nodes database 32, and labeling the infected node as having a percentage of infection likelihood (e.g., 25%, 50%, 100%, and so forth). Once all the infected nodes 18 have been labeled, as shown in FIG. 4, a pathway 30 that passes through each of the infected nodes can be determined.

Figure 3:
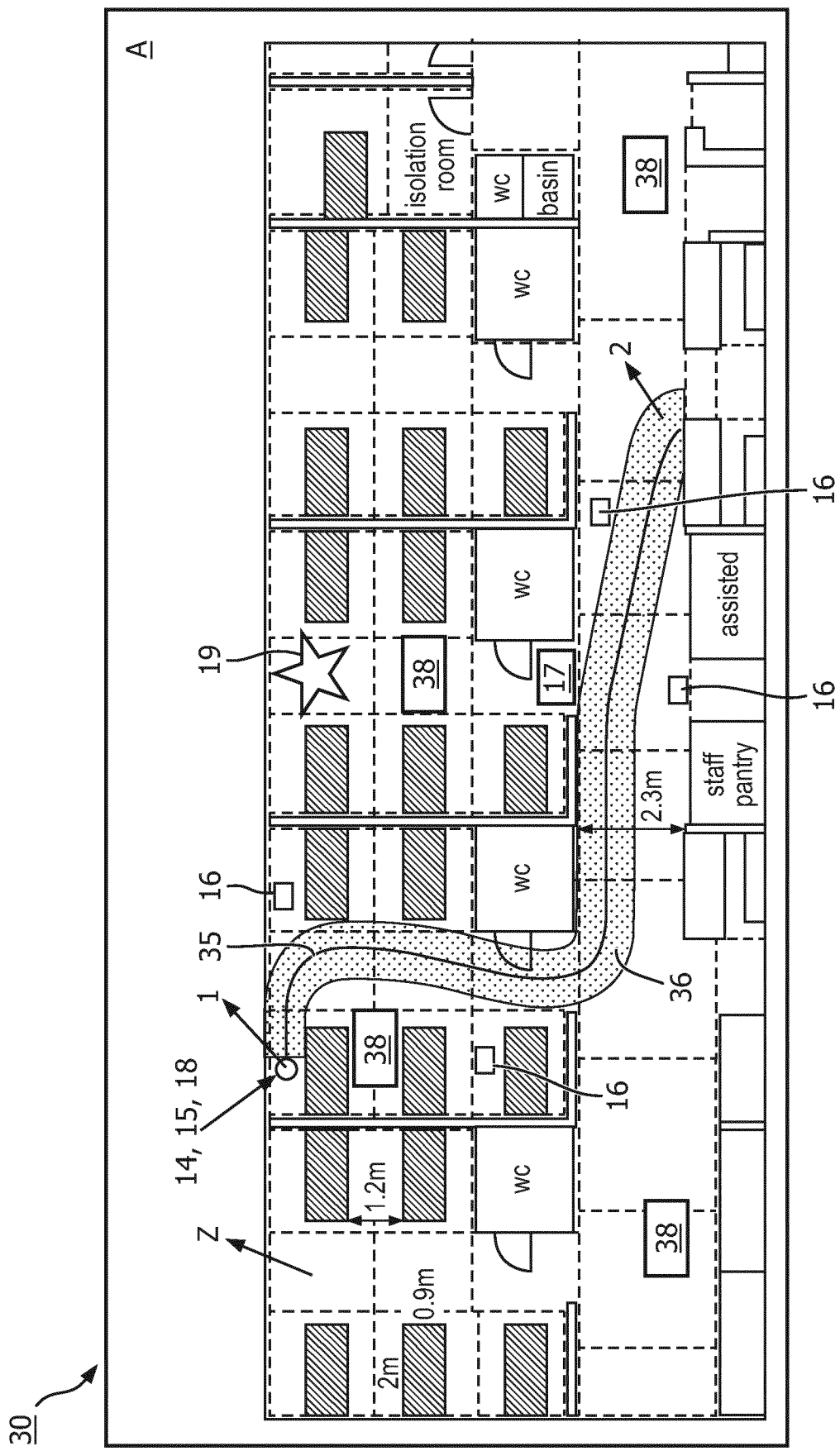
FIG. 3 illustratively shows an example use of the tracking system of FIG. 1.

FIG. 3 shows an example of the map 30 (or one floor of the map 30 in the case of a multi-floor map). The map 30 shows several zones Z (delineated by dashed lines) in which a tag reader 16 or beacon 17 may be located. Each zone Z represents a spatial area within which a tag 14 can be detected and localized by the RTLS 12. Said another way, the RTLS 12 can identify, at any given time, within which zone Z a given tag is located. As shown in FIG. 3, the tag readers 16 track the location of a corresponding node 18 at a first location 1 in a first zone to a second location 2 in a second zone. A pathway 35 is then determined and mapped between the first and second locations. In general, the determination of the pathway 35 is made based on the time series of locations of the tag 14 corresponding to the tracked node 18; however, additional pathway approximation processing may be employed for example, if the node 18 traverses an area that is not covered by the RTLS 12, then processing may be employed to interpolate the pathway 35 in the area not covered by the RTLS 12, e.g. assuming an average speed of the node 18 through the uncovered area. In other examples, the pathway 35 can be smoothed to more closely represent a person's movement.

At 104, an infectious zone 36 is computed on the map 30 along the pathway 35 using the infectious transmission information stored in the pathogen database 34. As shown in FIG. 3, an infectious zone 36 of approximately 1 m is marked out on either size of the pathway 35. The 1 m boundary is based on the criteria defined by the WHO for preventing the spread of infections. The width of the infectious zone 36 around the pathway 35 may be adjusted based on various factors, such as the time the infected node 18 spends in each map zone (the infectious zone 36 may be widened if the infected node 18 spends more time in a given map zone), or based on the airborne residency of the particular pathogen whose transmission is being tracked (e.g., the infectious zone 36 may be widened if the pathogen has a longer airborne residency, or may be narrowed if the pathogen has a shorter airborne residency or cannot be transmitted by the airborne pathway).

The adjustment can compensate for the possibility that certain infectious areas will be missed. In order to prevent this a user can specify a larger safety margin than the 1 m specified by the WHO. This would reduce or eliminate the chances of missing individuals who have been infected, thereby resulting in lower false negatives. (On the other hand, this action increases the chances of identifying unaffected individuals as infected individuals, thereby increasing false positives). The RTLS 12 also allow previously collected location data to be post-processed using different danger zone thresholds in order to compute different risk models which identify which individuals might be infected or be responsible for spreading infection.

At 106, for each node 18 contacting the infectious zone 36, the infection likelihood of the contacting node in the nodes database 28 is adjusted based on at least the infectious transmission information for the tracked pathogen and designating the contacting node as an infected node if the updated infection likelihood of the contacting node satisfies the infected criterion. A "contacting node" is one which whose location intersects the infectious zone 36 in a time interval over which the infectious zone 36 is deemed to be contaminated by the tracked pathogen. The time interval for pathogen transmission depends on the residency of the pathogen contamination on surfaces of the mobile object (for mobile object nodes) or on residency of pathogen contamination in the air or on surfaces in the case of a map zone node. Likewise, in the case of a node representing a person, there is usually an asymptomatic incubation period during which the person, having become infected, is contagious but does not exhibit any symptoms. If this incubation period passes without the person showing symptoms, then it may be concluded the person was not infected, and the node infection likelihood can be reset to zero.

To account for pathogen contamination residency time, in some embodiments, a time-dependent infection likelihood value is determined, for each node 18 in a list of nodes, in which the corresponding node is determined to have an infection likelihood which decreases to zero over time, with the likelihood reaching zero at the end of the incubation period for a human node (assuming the human remains asymptomatic) or at the end of the pathogen contamination lifetime for a mobile object or map zone node. In the case of a human node, if the human becomes symptomatic then the infection likelihood for that human node can be reset to one (certainly infected) and this unity infection likelihood can be propagated back in time to the point in time the human node acquired the infection (e.g. came into contact with the infectious zone 36). The infection likelihood of the nodes 18 decreases over time, and ultimately can end up at zero. In other examples, the time-dependent value is set to zero upon receiving an indication that the corresponding node 18 is no longer infectious (e.g. after passage of the incubation period with the person remaining asymptomatic, or after passage of the pathogen residency time on a surface or as airborne contamination).

In further embodiments, the time-dependent value of at least one of the nodes 18 is increased upon receiving, from one of the tag readers 16, multiple measurements that the pathway 32 between two of the corresponding nodes tracked by the tag reader remains unchanged. In other words, when a node 18 has stopped moving (e.g., when the node is a patient being moved through the hospital and the medical professional moving the patient stops for a moment), the distance between the corresponding tag 14 (or 15) and tag reader 16 (or the beacon 17 and the communication system 19) is the same. When this occurs, the time-dependent value is increased to make sure the RTLS 12 knows when the node 18 (i.e., the patient) is moving again. This is illustrated in FIG. 4. When the RTLS 12 detects that a node 18 has not emerged from a zone within a particular pre-defined time (that is, specified for that particular zone) the infectious zone 36 is extended to cover the entire area, as shown by enlarged zones Y.

In other embodiments, the RTLS 12 includes monitoring of usage of sanitary stations 38 disposed in the monitored area A, and the map 30 includes locations of the sanitary stations monitored by the RTLS. In this embodiment, the adjusting of the infection likelihood of the contacting node 18 in the nodes database 32 is further based on monitored usage of a sanitary station 38 at contact with the infectious zone 36.

In further embodiments, the adjusting of the infection likelihood of the contacting node 18 in the nodes database 32 is functionally dependent on several factors, including at least a distance between two nodes; air flow characteristics between two nodes; a time passed since one of the nodes was last in contact with the pathogen of interest; a type of surface of the node, a temperature in the vicinity of the node; a humidity value in the vicinity of the node; an order of node from the node which is considered to be the original source of infection; a number of times that the nodes have encountered each other since first getting infected; and an execution of hygiene regime.

Figure 5:
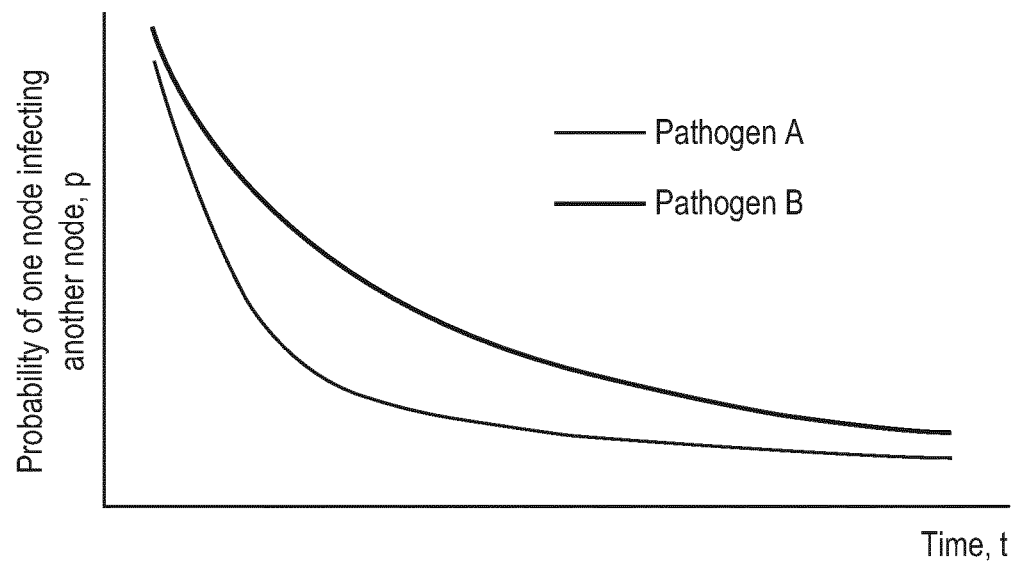
FIG. 5 shows a graph of data related to pathogens tracked by the tracking system of FIG. 1.

For example, as the RTLS 12 monitors the location of all nodes 18 in real-time, it continuously computes checks to see which pair of nodes should be connected by an edge and, if so, the at least one electronic processor 22 is programmed to assign a weight to the edge. The weight assigned to a node 18 corresponds to the probability that one node can infect the other. If both nodes 18 are in a position to infect each other, the edge is assigned the higher probability, i.e. weight. An edge is assigned between two nodes if the probability of one node infecting another is higher than a particular threshold p, where p (the weight assigned to the edge) is computed as follows:

$$p = f(d, a, t, s, T, H, o, i, h), \qquad (1)$$

where d: is a distance between the two nodes (i.e., a closest possible distance between the nodes); a is air flow characteristics (e.g. air velocity/pressure/etc.) between two nodes if they are connected through a common HVAC system; t is a time that has passed since the node was last in contact with the pathogen of interest; s is a type of surface (e.g. non-porous/textile/etc.) that predominantly defines the node; T is a temperature in the vicinity of the node; H is a humidity in the vicinity of the node; o is an order of node from the node which is considered to be the original source of infection; i is a number of times that the nodes have encountered each other since first getting infected; and h is an execution of hygiene regime (e.g. when a nurse uses a hand sanitizer, a room is disinfected, etc.). FIG. 5 shows a graph illustrating how p might vary over time (t) for different pathogens, given specific values for d, a, s, T, H, o, i and h. As shown in FIG. 5, the "top" curve is data for a first pathogen A, and the "bottom" curve is data for a second pathogen B.

Figure 6:
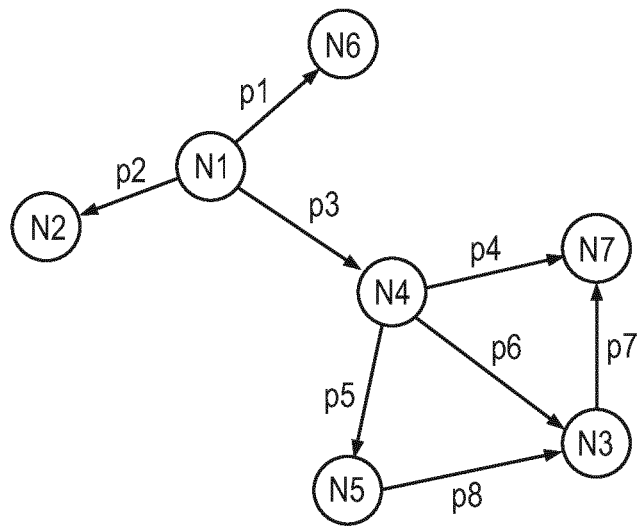
FIG. 6 shows a graph showing data of probabilities of nodes having pathogens tracked by the tracking system of FIG. 1.

Once a weight has been assigned to every edge, the system 10 generates a weighted directed graph, describing the probability P that each node N can infect another node, as shown in FIG. 6. The system 10 computes the weights on a continuous basis as real-time data streams in from the RTLS 12 installation. In some instances, an edge between two nodes might disappear (e.g., when the time that the infectious pathogen is outside the body exceeds a particular duration, when an infected entity executes a hygiene protocol such as when a nurse is infected through contact with infected washes hands with hand sanitizer, and so forth).

At 108, a list of nodes 18 with likelihoods of infectious areas can be displayed on the display device 26 for viewing by a medical professional. In some examples, the list of nodes include the nodes 18 with infection likelihoods that satisfy the infected criterion.

EXAMPLE

The following are two example algorithms, implemented on the electronic processor 22, to perform the disclosed operations:

Example 1 (For Contact and Droplet Precautions)

Nurse N1 enters Room R1 to meet Patient P1 lying on Bed B1.
N1 is in charge of taking care of P1
P1 is suffering from a currently undetected infectious medical condition, M1 involving Pathogen PG1.
PG1 can only be spread via contact, i.e. not via Droplets or Airborne transmission.
PG has a known lifetime of 5 days outside the body under certain conditions (e.g. certain temperature, humidity, etc.)
N1 wheels out P1 to another department for some tests in a Wheelchair, W1.
System monitors all entities that are either in the same zone or within 1 m of P1, N1 and W1 and stores location information of all tagged entities in the hospital on the server.
30 minutes after N1 and P1 have left R1, Nurse N2 enters Room and happens to make physical contact with B1 momentarily and leaves R1.
P1 is not the responsibility of N2.
1 day later P1 develops symptoms which correspond to condition M1.
3 days later, N1 and N2 are found to be suffering from symptoms corresponding to condition M1
While it is obvious to the Infection Control Manager, I1 that N1 caught the infection from P1, it is not clear how N2 also caught the infection.
Parameters are entered into the system. System forms directed graph.
Directed graph shows that an edge exists between B1 and N2.
Edges also exist which contain B1, P1, N1, W1 and N2
All assets sharing edges with B1, P1, N1, W1 and N2 are disinfected.
All persons sharing edges with B1, P1, N1, W1 and N2 are quarantined and/or prescribed appropriate treatment.

Example 2 (For Airborne Precautions)

Patient P1 is lying on Bed B1 in Room R1.
P1 is suffering from a currently undetected infectious medical condition, M1 involving Pathogen PG1.
PG1 can be spread via Airborne transmission.
PG1 has a lifespan of 5 hours outside the body.
Nurse N2 enters Room R2 to pick up some supplies 1 hour after P1 has been placed in R1.
Rooms R1 and R2 share ventilation
Nurse N2 inhales PG1 in R2
N2 develops M1 after 24 hours.
Parameters are entered into the system. System forms directed graph.
Directed graph shows that an edge exists between P1 and N2 due to shared ventilation between R1 and R2.
P1 is moved to a room with isolated ventilation and N2 is quarantined.

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An infectious disease transmission tracking system, comprising:
   a real-time locating system (RTLS) configured to track locations of tags in a monitored area;
   at least one electronic processor in operative communication with the RTLS to receive locations of tags in the monitored area; and
   a non-transitory storage medium storing:
      a map of the monitored area;
      a nodes database storing information on nodes wherein each node is a person, a mobile object, or a map zone and the nodes database stores information on the nodes including at least (i) an identification of each node as a person, a mobile object, or a map zone, (ii) an identification of a tag associated with each node that is identified as a person or a mobile object, (iii) locational information on the map for each node that is identified as a map zone, and (iv) an infection likelihood for each node with respect to a tracked pathogen;
      a pathogen database storing infectious transmission information for at least the tracked pathogen including one or more transmission modes for the tracked pathogen and at least one node residency time for the tracked pathogen; and
      instructions readable and executable by the at least one electronic processor to perform an infectious disease transmission tracking method including:
         computing a pathway on the map of at least one infected node using locations of the tag associated with the infected node received from the RTLS wherein an infected node has a non-zero infection likelihood respective to the tracked pathogen which satisfies an infected criterion;
         computing an infectious zone on the map along the pathway using the infectious transmission information stored in the pathogen database;
         for each node contacting the infectious zone, adjusting the infection likelihood of the contacting node in the nodes database based on at least the infectious transmission information for the tracked pathogen and designating the contacting node as an infected node if the updated infection likelihood of the contacting node satisfies the infected criterion.

2. The system of claim 1, wherein the at least one electronic processor is further programmed to:
   display, on a display device, a list of nodes with infection likelihoods that satisfy the infected criterion.

3. The system of claim 2, wherein the at least one electronic processor is further programmed to:
   determine, for each node in the list of nodes, a time-dependent value in which the corresponding node is determined to have an infection likelihood of zero.

4. The system of claim 3, wherein at least one electronic processor is further programmed to:
   set the time-dependent value to zero upon receiving an indication that the corresponding node is no longer infectious.

5. The system of claim 1, wherein the RTLS includes one of:
   (1) radiofrequency identification (RFID) tags and RFID tag readers; or
   (2) tags including an infrared (IR) receiver and a radiofrequency (RF) transceiver; a monitor configured to transmit IR signals throughout the monitoring area and output IR signals with unique IDs sensed by the tags, and an RF tracking communication station 44), operative to read IR IDs sensed by the tags.

6. The system of claim 2, wherein:
the RTLS includes monitoring of usage of sanitary stations distributed through the monitored area;
the map includes locations of the sanitary stations monitored by the RTLS; and
the adjusting of the infection likelihood of the contacting node in the nodes database is further based on monitored usage of a sanitary station at contact with the infectious zone.

7. The system of claim 1, wherein the adjusting of the infection likelihood of the contacting node in the nodes database is functionally dependent on at least a distance between the infected node and the contacting node and a time passed since the infected node was in contact with the tracked pathogen.

8. The system of claim 1, wherein the adjusting of the infection likelihood of the contacting node in the nodes database is functionally dependent on at least one of a type of surface of the infected node wherein the infected node is a mobile object or a map zone, a temperature in the vicinity of the node; and a humidity value in the vicinity of the node.

9. The system of claim 1, wherein the adjusting of the infection likelihood of the contacting node in the nodes database is functionally dependent on at least an order of node from the node which is considered to be the original source of infection; a number of times that the nodes have encountered each other since first getting infected; and an execution of hygiene regime.

10. The system of claim 7, wherein the adjusting of the infection likelihood of the contacting node in the nodes database is determined by the equation:

$$p=f(d,a,t,s,T,H,o,i,h), \quad (1)$$

where d is a distance between two nodes; a is air flow characteristics between the two nodes; t is a time passed since one of the nodes was last in contact with the pathogen of interest; s is a type of surface of the node, T is a temperature in the vicinity of the node; H is a humidity value in the vicinity of the node; o is an order of node from the node which is considered to be the original source of infection; I is a number of times that the nodes have encountered each other since first getting infected; and h is an execution of hygiene regime.

11. The infectious disease transmission tracking system of claim 1, wherein the:
real-time locating system (RTLS) including tags and tag readers, wherein the tag readers are distributed through the monitored area and are configured to track locations of the tags in the monitored area; and
wherein the adjusting of the infection likelihood of the contacting node in the nodes database is determined by the equation:

$$p=f(d,a,t,s,T,H,o,i,h), \quad (1)$$

where d is a distance between two nodes; a is air flow characteristics between the two nodes; t is a time passed since one of the nodes was last in contact with the pathogen of interest; s is a type of surface of the node, T is a temperature in the vicinity of the node; H is a humidity value in the vicinity of the node; o is an order of node from the node which is considered to be the original source of infection; I is a number of times that the nodes have encountered each other since first getting infected; and h is an execution of hygiene regime.

12. A non-transitory computer-readable storage medium, comprising:
a map database storing a map of a monitored area;
a nodes database storing information on nodes wherein each node is a person, a mobile object, or a map zone and the nodes database stores information on the nodes including at least (i) an identification of each node as a person, a mobile object, or a map zone, (ii) an identification of a tag associated with each node that is identified as a person or a mobile object, (iii) locational information on the map for each node that is identified as a map zone, and (iv) an infection likelihood for each node with respect to a tracked pathogen;
a pathogen database storing infectious transmission information for at least the tracked pathogen including one or more transmission modes for the tracked pathogen and at least one node residency time for the tracked pathogen; and
instructions readable and executable by at least one electronic processor to perform an infectious disease transmission tracking method including:
receiving, from one or more tag readers of a real time location system (RTLS), locations of one or more tags of the RTLS in the monitored area;
computing a pathway on the map of at least one infected node using locations of the tag associated with the infected node received from the RTLS wherein an infected node has a non-zero infection likelihood respective to the tracked pathogen which satisfies an infected criterion;
computing an infectious zone on the map along the pathway using the infectious transmission information stored in the pathogen database;
for each node contacting the infectious zone, adjusting the infection likelihood of the contacting node in the nodes database based on at least the infectious transmission information for the tracked pathogen and designating the contacting node as an infected node if the updated infection likelihood of the contacting node satisfies the infected criterion.

13. The non-transitory computer-readable storage medium of claim 12, wherein the infectious disease transmission tracking method further includes:
controlling, with the at least one electronic processor, a display device to display a list of nodes with infection likelihoods that satisfy the infected criterion.

14. The non-transitory computer-readable storage medium of claim 13, wherein the infectious disease transmission tracking method further includes:
determining, for each node in the list of nodes, a time-dependent value in which the corresponding node is determined to have an infection likelihood of zero.

15. The non-transitory computer-readable storage medium of claim 13, wherein the infectious disease transmission tracking method further includes:
adjusting the infection likelihood of the contacting node in the nodes database based on monitored usage of a sanitary station in the monitoring area at contact with the infectious zone.

* * * * *